Sept. 6, 1966 A. CHABERT Plant Pat. 2,669
ROSE PLANT
Filed Sept. 23, 1965
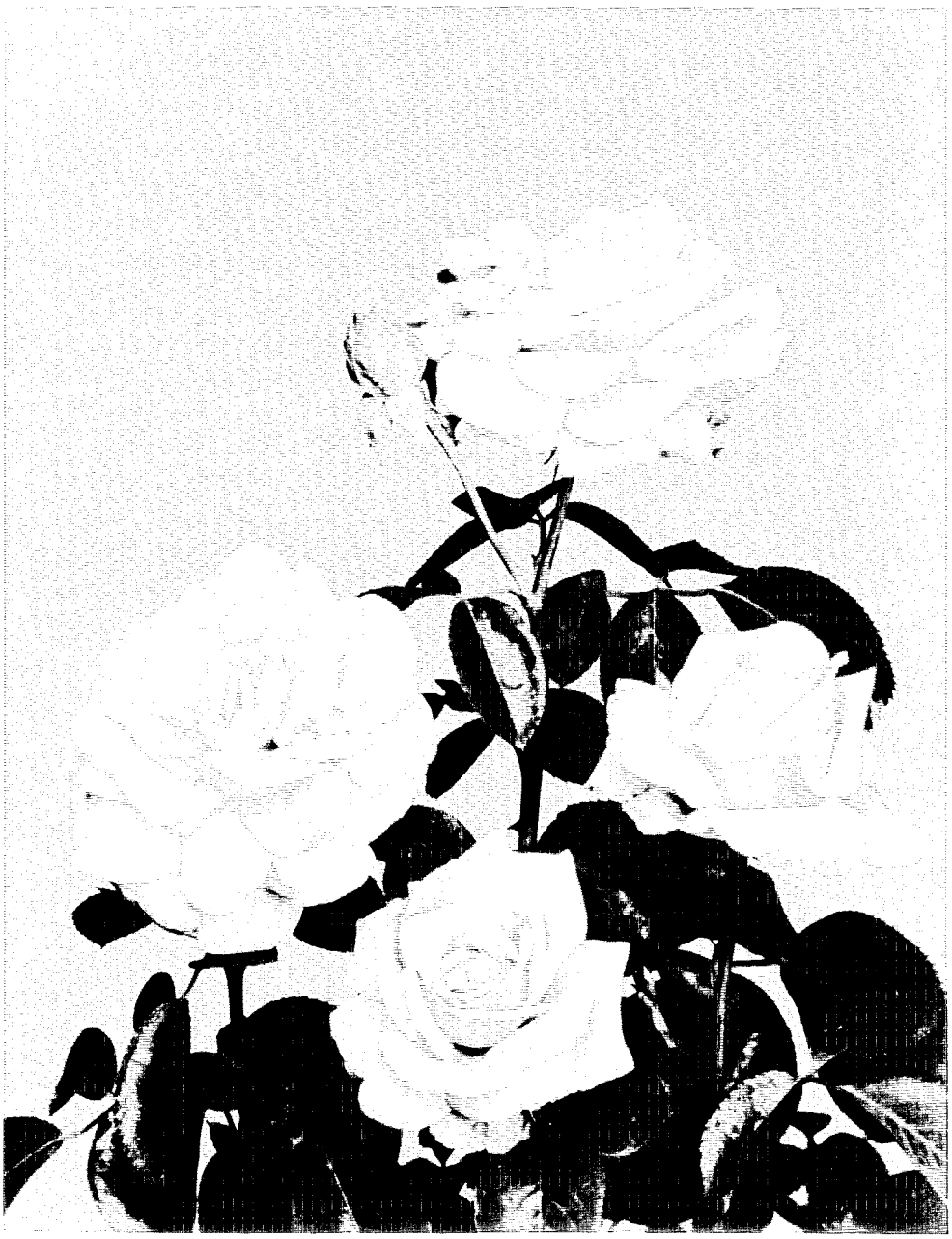
Inventor.
Andre Chabert
By: Robb & Robb
Attorneys.

United States Patent Office

Plant Pat. 2,669
Patented Sept. 6, 1966

2,669
ROSE PLANT

Andre Chabert, Paris, France, assignor, by mesne assignments, to Armstrong Nurseries, Inc., Ontario, Calif., a corporation of California

Filed Sept. 23, 1965, Ser. No. 489,772
1 Claim. (Cl. Plt.—18)

The present invention relates to a new and distinct variety of rose plant of a class intermediate the floribunda and hybrid tea classes, which was originated by me by crossing an unnamed and unpatented variety derived from a cross of the variety known as "Holstein" (U.S. Plant Patent No. 395) and the variety known as "Bayadere" (unpatented) with the variety known as "Prelude" (unpatented).

The primary objective of this breeding was to produce a new and improved rose variety which bears lavender colored flowers. This objective was fully achieved, as evidenced by the following unique combination of characteristics which are outstanding in the new variety and which distinguish it from its parents, as well as from all other varieties of which I am aware:

(1) A more vigorous plant habit than other lavender flowered varieties;

(2) Attractive, dark green, leathery, glossy, and mildew resistant foliage;

(3) Good floriferousness, with flowers borne both singly and in small clusters on strong stems usually of medium length;

(4) Quite double flower petalage, said flowers being of medium size and good form; and (5) A distinctive and attractive bluish-lavender general color tonality of the flowers.

In comparison with its unnamed seed parent, the new variety has fewer petals, ranging from 35 to 45 petals, as distinguished from the flower petalage of this parent variety in which the flowers have petals ranging from 45 to 55 petals, and the new variety bears flowers both singly and in small clusters, whereas the flowers of this parent are usually borne in clusters ranging from 3 to 8 flowers per cluster.

As compared with its pollen parent "Prelude," the new variety has greater petalage ranging from 35 to 45 petals, as distinguished from only about 25 petals in the case of the flowers of this parent.

Asexual reproduction of my new variety by budding, as performed in France and also at Ontario, California, U.S.A., shows that the aforementioned characteristics and distinctions come true to form and are established and transmited through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "W") and Robert Ridgway's Color Standards and Nomenclature (hereinafter abbreviated as "R").

Type: Bush; outdoor; seedling; for cut flowers and for garden decoration.

Class: Intermediate floribunda and hybrid tea.

Breeding: Seedling.

*Seed parent.*—An unnamed seedling of "Holstein" ×"Bayadere."

*Pollen parent.*—"Prelude."

Propagation: Holds its ditinguishing characteristics through succeeding propagations by budding.

Where propagated: Ontario, California, U.S.A., and Paris, France.

*Flower*

Locality where grown and observed: Ontario, California, U.S.A.

Flowers borne: Usually singly, but sometimes 3 or 4 to stem; in irregular clusters; on strong stems of medium length.

Quantity of bloom: Free, outdoors.

Continuity: Nearly continuous during growing season.

Fragrance: Slight.

Bud:

*Peduncle.*—Average length; from average caliper to heavy; usually smooth with few to several small stipitate glands and none to few small prickles. Color—near Kildare Green, Plate XXXI "R," overlaid with near Army Brown, Plate XL "R" on side exposed to the sun.

*Before calyx breaks.*—Size—from small to medium. Form—short; between ovoid and globular.

*As calyx breaks.*—Color—near Erythrite Red, Plate 0027, page 190 "W."

*Sepals.*—Inner surface—with fine, wooly tomentum. Margins of alternate sepals—lined with fine, wooly tomentum. Margins of others—with several to many small stipitate glands and small slender foliaceous parts, with sepals sometimes having foliaceous appendages extending up to ¼ of sepal length. Outer surface of sepals—usualy smooth, but sometimes with few small stipitate glands.

*As first petal opens.*—Size—from small to average. Form—from short to medium length; between ovoid and globular. Color: Outside—near Spiraea Red, Plate 025/1, page 112 "W," blending with near Magenta Rose, Plate 027/3, page 113 "W" toward base of petal; inside—near Erythrite Red, Plate 0027/3, page 190 "W," blending with near Rhodamine Pink, Plate 527/3, page 138 "W" toward base of petal.

*Opening.*—Opens up well.

Bloom:

*Size (when fully open).*—Average; from 3½ inches to 4½ inches.

*Petalage.*—Double; from 35 to 45 petals, plus 2 to 8 petaloids; arranged irregularly.

*Form.*—High-centered at first but becoming cupped to high-centered; petals being at first tightly cupped, with tips rolled outward, but later becoming more loosely cupped at maturity, with tips rolled outward; outside and intermediate petals of both newly opened and 3-days open flowers usually rolled outward both along edges and apex of petal, with petaloids in center of open flower usually arranged so stamens and pistils are hidden.

Petals:

*Texture.*—Medium thickness; soft.

*Appearance.*—Inside—satiny. Outside—satiny.

*Shape.*—Outside—between round and broadly obovate, with apex flat and sometimes with one or 2 notches. Intermediate—between round and obovate, with apex rounded and sometimes with one or 2 notches. Inside—between round and broadly obovate, with apex rounded.

This desription of a newly opened flower was made from a rose grown outdoors during the month of September at Ontario, California, U.S.A.:

*Color.*—Outer petal: Outside surface—near Fuchsine Pink, Plate 627/3, page 78 "W," with area along apex and edges of petal usually near Magenta Rose, Plate 027/1, page 113 "W"; inside surface—between Magenta Rose, Plate 027/3, page 113 "W" and Rhodamine Pink, Plate 527/3, page 138 "W." Intermediate petal:—Outside surface—between Fuchsine Pink, Plate 627/3, page 78 "W" and Rhodamine Pink, Plate 527/3, page 138 "W," with small area along edges of petal sometimes near Fuchsine Pink, Plate 627/1, page 78 "W"; inside surface—between Magenta Rose, Plate 027/3, page 113 "W" and Rhodamine Pink, Plate 527/3, page 138 "W." Inner petal: outside surface—between Fuchsine Pink, Plate 627/3, page 78 "W" and Rhodamine Pink, Plate 527/1, page 138 "W," with petal usually having vegetative streaks between white and Fuchsine Pink, Plate 627/3, page 78 "W" from base toward apex; inside surface—between Magenta Rose, Plate 027/3, page 113 "W" and Rhodamine Pink, Plate 527/2, page 138 "W."

This description was made from a rose that was open for three days outdoors during the month of September at Ontario, California, U.S.A.:

*Color.*—Outer petal: Outside surface—near Amaranth Rose, Plate 530/3, page 139 "W," with area along edges and apex of petal near Mallow Purple, Plate 630/1, page 79 "W"; inside surface—between Magenta Rose, Plate 027/3, page 113 "W" and Amaranth Rose, Plate 530/3, page 139 "W." Inner petal: Outside surface—near Amaranth Rose, Plate 530/2, page 139 "W," with area along edges and apex of petal near Mallow Purple, Plate 630/2, page 79 "W"; inside surface—near Amaranth Rose, Plate 530/3, page 139 "W," with area along edges and apex near Amaranth Rose, Plate 530/1, page 139 "W."

*General color effect.*—Newly opened flower—between Magenta Rose, Plate 027/3, page 113 "W" and Rhodamine Pink, Plate 527/2, page 138 "W." 3-days open—between Amaranth Rose, Plate 530/3, page 139 "W" and Magenta Rose, Plate 027/3, page 113 "W."

*Behavior.*—Drop off cleanly.

*Flower longevity.*—On bush in garden—4 or 5 days in October. Cut roses grown outdoors and kept at living room temperature—3 or 4 days in October.

*Reproductive organs*

Stamens: From few to average number; arranged regularly about pistils; a few mixed with petaloids.

Filaments: From short to medium length (3 mm. to 8 mm. long); most with anthers.

Anthers: From small to medium size; all open approximately at once. Color: Upper side—margins near Maize Yellow, Plate 607, page 69 "W" with remainder near Primrose Yellow, Plate 601/3, page 65 "W"; under side—margins near Maize Yellow, Plate 607, page 69 "W," with remainder near Primrose Yellow, Plate 601/3, page 65 "W."

Pollen: From sparse to moderate quantity. Color—near Tangerine Orange, Plate 9/1, page 9 "W."

Pistils: Average number (approximately 70).

Styles: Uneven; from short to average length; very thin caliper; bunched. Color—upper half of style near Fuchsine Pink, Plate 627/3, page 78 "W," with remainder near Primrose Yellow, Plate 601/3, page 65 "W."

Stigma: Color—near Empire Yellow, Plate 603/2, page 66 "W."

Ovaries: Usually all enclosed in calyx.

Hips: None observed.

Seeds: None Observed.

*Plant*

Foliage:

*Leaves.*—Compound of usually 3–7 leaflets; normal abundance; medium size; leathery; glossy.

*Leaflets.*—Shape—broadly oval, with apex acute. Base—round. Margin—simply serrate. Color: Mature—upper surface—near Cress Green, Plate XXXI "R"; under surface—near Chromium Green, Plate XXXII "R." Young—upper surface—near Light Yellowish-Olive, Plate XXX "R"; under surface—near Rainette Green, Plate XXXI "R."

*Rachis (the supporting stem of the compound leaf).*—Average size. Upper side—grooved; with few to several small stipitate glands on edges. Under side—smooth; with none to few small prickles.

*Stipules.*—From short to medium length; medium width; with short to medium length points turning out at an angle usually less than 45°.

*Disease resistance.*—Better than average resistance to mildew as compared with other varieties grown under comparable conditions at Ontario, California, U.S.A.

Growth:

*Habit.*—Upright-spreading; much branched.

*Growth.*—Moderately vigorous.

*Canes.*—Medium caliper.

*Main stems.*—Color—near Oil Green, Plate V "R." Large prickles—from several to many; from short to medium length; almost straight; with short, narrow base. color—near Wood Brown, Plate XL "R." Small prickles—few. color—near Wood Brown, Plate XL "R." Hairs—none.

*Branches.*—Color—near Light Cress Green, Plate XXXI "R." Large prickles—from several to many; from medium length to long; almost straight; with narrow base of medium length; color—near Ecru Olive, Plate XXX "R." Small prickles—from none to few; color—near Ecru Olive, Plate XXX "R." Hairs—none.

*New shoots.*—Color—near Biscay Green, Plate XVII "R," overlaid with near Rainette Green XXXI "R" on side exposed to the sun. Large prickles—from few to several; medium length; hooked slightly downward; with short, narrow base; color—near Ocher Red, Plate XXVII, "R." Small prickles —from none to few, color—near Ocher Red, Plate XXVII "R." Hairs—none.

I claim:

A new and distinct variety of rose plant intermediate of the floribunda and hybrid tea classes, substantially as herein shown and described, characterized particularly as to novelty by the unique combination of a more vigorous plant habit than other lavender flowered varieties, attractive, dark green, leathery, glossy, and mildew resistant foliage, good floriferousness, with flowers borne both singly and in small clusters on strong stems usually of medium length, quite double flower petalage, said flowers being of medium size and good form, and a distinctive and attractive bluish lavender general color tonality of the flowers.

No references cited.

ABRAHAM G. STONE, *Primary Examiner.*

R. E. BAGWILL, *Assistant Examiner.*